United States Patent [19]

Schmidhammer et al.

[11] Patent Number: 4,754,088

[45] Date of Patent: Jun. 28, 1988

[54] PROCESS FOR OXYCHLORINATION OF ETHYLENE

[75] Inventors: Ludwig Schmidhammer, Haiming; Peter Hirschmann, Burghausen, both of Fed. Rep. of Germany; Herbert Patsch, Braunau, Austria; Rudolf Strasser, Burghausen, Fed. Rep. of Germany

[73] Assignee: Wacker-Chemie GmbH, Fed. Rep. of Germany

[21] Appl. No.: 13,285

[22] Filed: Feb. 11, 1987

[51] Int. Cl.⁴ .............................................. C07C 17/02
[52] U.S. Cl. .................................. 570/247; 570/241; 570/243; 570/245
[58] Field of Search ............... 570/247, 241, 243, 245

[56] References Cited

U.S. PATENT DOCUMENTS 4,046,822  9/1977  Severino .............................. 570/241

*Primary Examiner*—Howard T. Mars
*Attorney, Agent, or Firm*—Bierman and Muserlian

[57] ABSTRACT

In a process for preparation of 1,2-dichloroethane by chlorination of ethylene-containing reaction vent gases from the oxychlorination of ethylene in the presence of a catalyst carrier impregnated with metal compounds wherein the waste from the oxychlorination stage are chlorinated, the improvement comprising preheating the ethylene-containing waste gases to at least 50° C. and then chlorinating the ethylene at 100° to 300° C. at a pressure of 1 to 7 bar with a space velocity of 100 to 5000 $h^{-1}$ related to standard conditions in the presence of at least one metal compound selected from the group consisting of chlorides and oxides of manganese, nickel and cobalt supported on a catalyst carrier with reduced formation of oxychlorinated by-products.

6 Claims, No Drawings

PROCESS FOR OXYCHLORINATION OF ETHYLENE

STATE OF THE ART

It is known that 1,2-dichloroethane (EDC) can be formed by oxychlorination of ethylene so that, in a first stage, excess ethylene, hydrogen chloride and excess oxygen, in the form of pure air or of oxygen-enriched air, are reacted at 220° C. to 350° C. and an absolute pressure of 3 to 8 bar in the presence of a conventional oxychlorination catalyst by appropriate adjustment of the ratios of the amounts of starting materials (British Pat. No. 1,104,666 and EP Application No. 146,925). After condensing out the reaction products which can be separated into an organic, crude EDC-containing phase and an aqueous, unreacted hydrogen chloride-containing phase, and after subsequent prewarming to at least 50° C. to prevent dew point corrosion, the ethylene-containing gases remaining after the above stage are mixed with chlorine in approximately stoichiometric amounts, relative to the ethylene contained in the residual gas stream. The gas mixture thus obtained is then converted in a subsequent second stage at 80° C. to 320° C. in the presence of activated aluminum oxide as catalyst, further crude EDC being produced. By a two-stage condensation, the first stage being carried out at 20° C. to 40° C. and the second stage at about −25° C., the EDC contained in this reaction mixture can be separated off virtually quantitatively from the remaining residual gas stream, now almost free of ethylene (British Pat. No. 1,230,604). The combined crude EDC streams of both reaction stages are then heated in an acidic and alkaline washing system, and are subsequently subjected to distillative drying and purification.

In the said process route, overall not insignificant amounts of oxygen-and chlorine-containing by-products such as chloral or chloral hydrate and 2-chloroethanol, and, to a lesser extent 2,2-dichloroethanol and 2,2,2-trichloroethanol as well as 2,2'-dichlorodiethyl ether and bis-2-chloroethoxyethane are produced, besides crude EDC as the target product, in both the first reaction stage and in the second reaction stage. These oxygen-containing by-products are extremely troublesome since some of them are relatively difficult to separate from EDC [eg. chloral forms an azeotrope with EDC], and some consume large amounts of alkaline solutions for their hydrolytic decomposition.

If they are contained in pure EDC, they have a strongly inhibiting effect during EDC cleavage and promote the formation of by-products and coke. In addition, they are usually very corrosive and also considerably increase the chemical oxygen demand of the waste water from the reaction, since they partially pass over into the aqueous phase and are dissolved there. The formation of these troublesome by-products in the first reaction stage can only be influenced within very narrow limits due to firmly prespecified operating parameters or catalysts. Thus, chloral or chloral hydrate are formed in approximately equal parts in the first and second reaction stages, whereas the proportion of 2-chloroethanol and its homologues formed in the first reaction stage is only about 20% relative to the total yield.

Most of the 2-chloroethanol and its homologues are thus produced in the second reaction stage by reaction of ethylene with chlorine in the presence of water vapors, which are contained according to the tension, in the ethylene-containing residual gas stream from the oxychlorination stage. The formation of chloral and the other by-products is likewise causally connected with the reaction between water vapors and chlorine. Whereas chloral or chloral hydrate can easily be removed from the crude EDC by treatment with an alkaline solution, since it is spontaneously decomposed into chloroform and formate by the action of alkali, the purely extractive removal of 2-chloroethanol or its homologues from the crude EDC only succeeds to a very incomplete extent.

Since these chloroethanols can hardly be hydrolyzed under the conditions of a one-stage alkaline solution wash, about 10 washing stages, purely arithmetically, would have to be carried out successively to produce 99% removal of these chloroethanols from the crude product under the normally prevailing extraction conditions, for example in the case of a conventional chloroethanol concentration in the crude product or in the case of usual ratios of organic to aqueous phase of about 4 to 6:1 by volume, due to the prespecified distribution coefficient, for which the Nernst Law is fully valid. For economic reasons, however, only one alkaline solution washing stage is usually used, which is fully sufficient for complete separation of chloral and for neutralization of the crude product, but in which the chloroethanols are only washed out of the crude product to an extent of about 40%, relative to total yield in the two reaction stages. The use of several washing stages or an extraction column not only incurs relatively high capital and operating costs, but also increases the total amount of waste water, whereby the costs for waste water stripping and the subsequent biological work-up of the waste water also increase considerably. In addition, these oxygen-containing by-products reduce the conversion of ethylene and chlorine to EDC, i.e. they reduce the selectivity.

Numerous proposals have been made to suppress the formation of the by-products as far as possible, but some cannot be achieved in an economic fashion because of excessive costs, and some are only effective in narrow limits and can thus not be used generally, or are uneconomical per se because of increased oxygen consumption and poor yields and catalyst lives. The selectivities often also remain unsatisfactory.

Thus, it has already been proposed that, to suppress these side reactions, the water be separated completely from the ethylene-containing residual gases from the oxychlorination stage and only the residual gases together with chlorine be fed into the chlorination reactor after this. However, this process is very costly; for example, condensation of water vapors from the gas stream by deep cooling and chemical drying or by adsorption on suitable adsorbents are necessary, and consumes large amounts of energy, particularly through the cooling and reheating of the gas stream.

In contrast, Chem. Abstr., Vol. 90, 137243j teaches that the formation of chloral and chloroethanol can be reduced without loss of selectivity when the ethylene-containing waste gas stream from the oxychlorination stage, alone or as a mixture with stoichiometric amounts of chlorine, is pre-warmed to temperatures of 150° C. to 200° C. before the actual reaction on activated aluminum oxide as catalyst, that is to say before entering the reaction zone. Although the formation of these harmful, oxygen-containing by-products is thereby drastically reduced compared to the procedure of British Pat. No.

1,230,604, this effect only appears when the ethylene-containing residual gas stream from an oxychlorination, as described in British Pat. No. 1,104,666, for example, only contains 2 to 4% by volume of ethylene.

In contrast, if an oxychlorination is carried out at considerably increased throughputs, relative to the design capacity which have in the meantime become necessary for economic reasons, for example as in EP-A No. 146925, a residual gas stream containing about 5 to 12% by volume of ethylene is necessarily produced since, due to the use of oxygen-enriched air, the specific nitrogen ballast, relative to the total oxygen content of the oxygen source, is correspondingly lower and the ethylene content in the residual gas from the oxychlorination thus increases accordingly, even when comparable oxygen excesses are used in the oxychlorination. Similarly, the partial pressure of chlorine in the residual gas from the oxychlorination also increases thereby, since the chlorine must be added in approximately stoichiometric amounts to the ethylene present in the residual gas from the oxychlorination.

Under these conditions, however, it has been shown that the measure taught by Chem. Abs., Vol. 90, 137243j for reducing the undesired formation of by-products is no longer effective to the same extent since, by increasing the partial pressure of chlorine, more hypochlorous acid is necessarily produced, corresponding to the law of mass action, by interaction with water vapors. In the final analysis, this hypochlorous acid contributes to the formation of these undesired by-products by reaction with ethylene. In addition, relatively poor yields of ethylene and chlorine, and also, caused by this, lower selectivity, relative to the formation of EDC, are achieved in this process, since, very generally, the substitution reaction is favored at elevated temperatures.

In U.S. Pat. No. 4,142,893 it is proposed that, to specifically minimize the formation of 2-chloroethanol, hydrogen chloride be added to the ethylene-containing residual gas stream from an oxychlorination before reaction with stoichiometric amounts of chlorine on activated aluminum oxide as catalyst. Apart from the fact that this does not represent a feasible route for universal suppression of all undesired, oxygen-containing by-products, every expert knows that although the formation of hypochlorous acid as a precursor to the formation of 2-chloroethanol can be lessened by addition of hydrogen chloride, because of the law of mass action of the disproportionation reaction between chlorine and water, the hydrogen chloride added which does not take part in the reaction is partly lost via the waste gas and partly, as acid, via residual water condensed at $-25°$ C., causing the utilization of hydrogen chloride in the entire two-stage process to be considerably reduced.

According to Chemical Abstr. Vol. 87, 38838 p, the formation of chloral and 2-chloroethanol is suppressed to a relatively great extent when the chlorination of ethylene-containing residual gases from an oxychlorination is carried out in the presence of activated aluminum oxide which is impregnated with copper II chloride and/or iron III chloride and, additionally, with alkali metal or alkaline earth metal chlorides, the supported catalyst being used diluted with inert material, for example with α-aluminum oxide, quartz, silicon carbide, graphite or mixtures thereof. However, this process has only relatively modest success, above all regarding the suppression of the formation of 2-chloroethanol, since even low amounts of 2-chloroethanol contained in washed and neutralized crude EDC cause great corrosion, because of its high boiling point, in the distillative purification of crude EDC, since this residual amount of 2-chloroethanol accumulates in the bottoms of the column for the separation of the high-boiling materials and has an extremely troublesome effect, depending on the concentration present, in the further work-up of this distillation product. This is because 2-choroethanol, due to its high dipole moment, has a polarizing effect on hydrogen chloride formed by thermal decomposition of higher-boiling chlorinated hydrocarbon by-products in dry, organic bottoms of the column for high-boiling products, such that the hydrogen chloride is partly present in dissociated form and is thus very corrosive.

In addition, 2-chloroethanol reacts with hydrogen chloride, partly with elimination of water whereby the corrosion is increased. Besides this, only relatively moderate conversions of ethylene and low selectivities, with respect to the formation of EDC, and moderate EDC yields, relative to ethylene, are achieved using this process. This is because, as is known, copper II chloride and, above all, iron III chloride catalyze both the hydrochlorination of ethylene to ethyl chloride and also the substituting chlorination of EDC to worthless 1,1,2-trichloroethane, especially when the process is carried out in the gas phase. Furthermore, such carrier support catalysts have relatively short lives since copper II chloride and iron III chloride sublime off the carrier relatively quickly at elevated temperatures, due to their high volatility, and the carrier support catalyst is therefore gradually depleted of active substance. Although the addition of relatively small amounts of alkali metal or alkaline earth metal chlorides can inhibit the volatility of copper II chloride and iron III chloride to a certain extent, a gradual reduction of the partial pressure of these two active components is, however, only possible by addition of large amounts of alkali metal or alkaline earth metal chlorides with formation of defined eutectic mixtures, which, however, are themselves considerably less catalytically active than the pure active components.

OBJECTS OF THE INVENTION

It is an object of the invention to suppress the formation of by-products as much as possible, i.e. to reduce it substantially in an economic fashion and universally by reaction control, particularly in the second process stage, and thereby to simultaneously increase the selectivity of the reaction in the second stage with respect to the output of EDC, and also the conversions and, thus, also the ethylene- and chlorine-based yields.

This and other objects and advantages of the invention will become obvious from the following detailed description.

THE INVENTION

The novel process of the invention for preparation of 1,2-dichloroethane by chlorination of ethylene-containing reaction vent gases from the oxychlorination of ethylene in the presence of a catalyst carrier impregnated with metal compounds wherein the waste gases from the oxychlorination stage are chlorinated, the improvement comprises preheating the ethylene-containing waste gases to at least 50° C. and then chlorinating the ethylene at 100° to 300° C. at a pressure of 1 to 7 bar with a space velocity of 100 to 5000 h$^{-1}$ related to standard conditions in the presence of at least one metal compound selected from the group consisting of chlorides and oxides of manganese, nickel and cobalt supported on a catalyst carrier.

The improved process for the preparation of 1,2-dichloroethane by gas-phase chlorination of ethylene-containing residual gases in the presence of water vapors has now been found to avoid all the disadvantages mentioned, and the formation of all interfering oxygen- and chlorine-containing by-products, with high selectivities, EDC yields and chlorine and ethylene conversions. The process according to the invention is suitable for the gas-phase chlorination of residual gases from an oxychlorination having an ethylene content of 2 to 12% by volume, in which process ethylene and chlorine react virtually completely with one another to form EDC of high purity, and long catalyst lives are achieved.

The concentration of the heavy-metal chlorides and/or oxides employed in the invention on the catalyst carrier is preferably 1 to 30% by weight in each case, more preferably 5 to 15% by weight, particularly about 10% by weight, in each case relative to the carrier material where, in the case of the use of mixtures, the total amount of all heavy-metal chlorides and/or oxides used together must especially preferably not exceed 30% by weight relative to the carrier.

Activated aluminum oxide, aluminum oxide hydrate, silica gel, aluminum silicate, or mixtures thereof are preferably used as the catalyst carrier. The specific surface area, according to BET, of the catalyst carrier should preferably be 20 to 200 $m^2/g$. In a preferred embodiment, the carrier support catalyst can additionally also contain up to 20% by weight of copper II chloride and 0.5 to 10% by weight of alkali metal or alkaline earth metal chlorides or mixtures thereof, in each case relative to the carrier material.

These carrier catalysts are prepared in a fashion which is known per se, for example by impregnation. Thus, it is also possible to use as carrier material conventional fixed-bed oxychlorination catalysts which are impregnated with one or more of the heavy-metal chlorides and/or oxides used in the invention. The carrier support catalyst of the invention can be used undiluted or, alternatively, diluted with an inert material such as α-aluminum oxide, quartz, silicon carbide, graphite, ceramic sinter material or the like, the non-oxidizable substances being preferred here.

The carrier support catalyst can be used in any form such as spheres, pellets, rings, saddle-shapes or extrudates, i.e. any forms which hamper the carry-out of the catalyst and preferably only cause low losses in pressure and flow rates.

The process of the invention is not limited to particular oxychlorination conditions and can thus be used universally in combination with any oxychlorination process in which air, or oxygen-enriched air, and ethylene are used in excess, based on the stoichiometry with respect to hydrochloric acid. The gas stream from the oxychlorination is preferably first cooled down to such an extent that substantial condensation and separation of the organic reaction products and of the water of reaction, or washing-out of unreacted hydrochloric acid as near to quantitatively as possible, from the remaining, ethylene-containing residual gas stream are achieved. This residual gas stream then preferably contains about 2 to 12% by volume of ethylene, 1 to 3% by volume of oxygen, 75 to 85% by volume of nitrogen, 0.5 to 1.5% by volume of carbon monoxide, 0.5 to 1.5% by volume of carbon dioxide, 1 to 4% by volume of water vapors, 2 to 6% by volume of EDC and 0.1 to 0.5% by volume of ethyl chloride.

After pre-warming and approximately stoichiometric addition of chlorine based on the ethylene content of the residual gas from the oxychlorination, the gas mixture is reacted in the presence of the carrier support catalyst of the invention. When the reaction is complete, the reaction gases emerging from the vapor phase chlorination reactor are cooled, preferably to 20° C. to 40° C., whereupon partial condensation occurs and the condensed organic components of the gas stream are separated off and recovered. The remaining residual gas stream is then cooled, preferably to about −25° C., whereupon further organic material and residual water vapors condense out, and are subsequently fed to a waste gas combustion plant or to a waste gas purification plant.

Surprisingly, the amounts of all oxygen- and chlorine-containing by-products can be kept extremely low when using the catalyst of the invention, even when increased concentrations of ethylene, and thus also chlorine, are present, and the reaction of chlorine with ethylene to form EDC can be designed to be very selective, with high yield, although, as is known, the formation of oxygen- and chlorine-containing by-products is promoted and the substituting further chlorination of the EDC produced increased with increasing ethylene concentration in the residual gas from an oxychlorination due to the law of mass action, since, very generally, the control of the reaction temperature is rendered more difficult with increasing ethylene concentration and with the increase in the heat of reaction being evolved, which is associated with the latter. Besides this, the process of the invention involves a considerable technical advance since the carrier support catalysts of the invention ensure a very long life of several years.

In the following examples there are described several preferred embodiments to illustrate the invention. However, it is to be understood that the invention is not intended to be limited to the specific embodiments.

EXAMPLE 1

The heavy-metal chlorides and/or oxides, or mixtures thereof, with additional amounts of copper II chlorides and alkali metal or alkaline earth metal chlorides of Table 1, Nos. A to J were dissolved in water and the solution was then applied to the carrier materials of Table 1, Nos. A to J. The impregnation was carried out so that the salts and/or oxides were dissolved in just as much water as 950 ml of the individual carrier materials could absorb in each case to ensure that the active substance was thoroughly distributed and was present on the support material in the desired concentration range. In total, 950 ml of each of the various carrier support catalysts were prepared per experiment, and the catalysts were in each case dried, after the impregnation process, at 150° C. in a nitrogen stream until the weight remained constant.

The reactor comprised a vertical nickel tube of a length of 2 meters and an internal diameter of 26 mm which was heated using thermostatically-controlled heat exchange oil over a length of 180 cm and the reactor was charged in each case with 950 ml of catalyst. A 10 ml thick layer of inert material, e.g. ceramic Berl saddles, was located at each of the upper and lower ends of the reactor. The gas streams of Table 1, Experiment Nos. A to J, were fed successively, after appropriate water saturation and pre-warming, sometimes also with addition of HCl, together with stoichiometric amounts of chlorine, relative to the appropriate ethylene content, to the upper end of the reactor at atmospheric pressure and a heating jacket temperature of 135° C. and the reaction was initiated at an average temperature in the catalyst bed of about 170° to 200° C. After emerging from the lower part of the reactor, the reaction mixture was initially cooled in a water condenser, whereupon partial condensation occurred, and then was passed into a cold trap at −35° C., whereupon a further condensate was produced. The remaining amount of residual gas was discharged into the laboratory fume hood. The collected condensates were separated into an organic and an aqueous phase, and each was examined by gas chromatography for chloral or chloral hydrate, 2-chloroethanol, 2,2-dichloroethanol, 2,2,2-trichloroethanol, 2,2'-dichlorodiethyl ether and bis-2-chloroethoxyethane. The proportions by weight of the individual oxygen-containing chlorine compounds are reported in Table 1 under the heading "composition of the condensate" as the sum from the organic plus the aqueous phase.

COMPARISON EXAMPLE 1

The catalysts of the composition of Table 2, Nos. K to S, were prepared analogously to Example 1 and the reaction of the ethylene-containing gas streams of Table 2, Nos. K to S, with chlorine was carried out under the same conditions as described in Example 1, as was the condensation and the analysis of the condensates by gas chromatography, and also the evaluation under the heading "compositions of the condensates" in Table 2.

On comparison of the two tables, the superiority of the process of the invention compared to the prior art is clear. As can be seen very clearly from experiments L and M, in particular, on the one hand the increased pre-warming does not bring the same good effect as the process of the invention, and on the other hand, increased pre-warming no longer has a particularly great effect with respect to by-product suppression at relatively high ethylene contents. Experiments N and O also illustrate the superiority of the process of the invention compared to the process involving addition of hydrogen chloride, where, in this case, increased pre-warming has absolutely no additional effect. Experiments P to S show that both copper II chloride and, above all, iron III chloride greatly accelerate the hydrochlorination of ethylene, and also do not affect the suppression of by-products, particularly noticeable in the case of 2-chloroethanol, to the same good degree as the process of the invention.

It is furthermore surprising that the hydrochlorinating action of copper II chloride in the presence of the catalyst of the invention does not appear (see Experiments E and J).

EXAMPLE 2

The catalyst was prepared as in Example 1 by impregnating a spherical oxychlorination catalyst which contained 10% by weight of copper II chloride and 3.5% by weight of potassium chloride with 10% by weight of manganese II chloride. The prepared catalyst was then introduced into a chlorination reactor by the following loading pattern:

| | | |
|---|---|---|
| ⅓ of the upper reactor length: | 70% by vol. "Norton 704" + | 30% by vol. catalyst |
| ⅓ of the central reactor length: | 50% by vol. "Norton 704" + | 50% by vol. catalyst |
| ⅓ of the lower reactor length: | | 100% by vol. catalyst |

"Norton 704" is a commercially available inert diluent based on α-aluminum oxide and is likewise spherical. After reaction of 500 kmol/h of hydrogen chloride, 288 kmol/h of ethylene and 500 kmol/h of air which was enriched to contain 30% by volume of oxygen by addition of oxygen, and condensation of the reaction mixture according to DE-A-1,493,213, 9,800 m$^3$/h (based on standard conditions) of a residual gas stream of essentially the following composition was produced at an absolute pressure of 5 bar and a temperature of 45° C.:

7.5% by volume of ethylene
3% by volume of oxygen
2% by volume of water vapors
0.7% by volume of each of carbon monoxide and carbon dioxide
4% by volume of EDC vapor
0.5% by volume of ethyl chloride vapor, and
81.5% by volume of $N_2$.

This gas stream was initially pre-warmed to about 110° C. then mixed with 32.5 kmol/h of chlorine vapor (ethylene:chlorine molar ratio=1.003) and passed into a chlorination reactor. The reactor was provided, as a tube bundle-reactor, with a steam jacket in which steam at an excess pressure of 1.5 bar and warm water were used for heating to operating conditions or for cooling. The tubes of the reactor were packed with the catalyst described initially corresponding to the loading pattern shown above. The total reactor volume was 4000 liters and the space velocity, based on standard conditions (0° C, 1013 hPa) was thus about 2,630 h$^{-1}$. A reaction between ethylene and chlorine to form mainly 1,2-dichloroethane occurred in the reactor and the maximum temperature in the catalyst bed of this gas-phase chlorination process was 260° C. The gas mixture emerging from the reactor was successively cooled in two stages to 40° C. and −25° C. respectively, condensation occurring in both cooling stages. The 3,185 kg/h of condensates produced were separated from the gas stream and fed together to the EDC wash (together with crude EDC from the oxychlorination stage).

The remaining residual gas was fed under pressure control to a waste gas combustion plant and the combined condensates from both cooling stages had the following composition:

98.35% by weight 1,2-dichloroethane
0.50% by weight 1,1,2-trichloroethane
0.48% by weight ethyl chloride
0.005% by weight trans-1,2-dichloroethylene
0.018% by weight 1,1-dichloroethane
0.007% by weight cis-1,2-dichloroethylene
0.064% by weight chloroform
0.105% by weight carbon tetrachloride
0.38% by weight chloral
0.09% by weight 2-chloroethanol
0.005% by weight 2,2-dichloroethanol
0.0008% by weight 2,2,2-trichloroethanol
<5 ppm by weight 2,2'-dichlorodiethyl ether
<1 ppm by weight bis-2-chloroethoxyethane The 8,300 m³/h (based on standard conditions) waste gas stream reaching the combustion plant had the following composition:
94.5% by volume nitrogen
0.8% by volume carbon monoxide
0.8% by volume carbon dioxide
3.5% by volume oxygen
0.17% by volume ethyl chloride
0.17% by volume 1,2-dichloroethane
0.05% by volume hydrogen chloride
0.01% by volume ethylene
5 ppm by volume chlorine From this, conversion of 99.99%, based on chlorine, or 99.8% based on ethylene, were calculated and the yields were 98.6% of theory, based on ethylene, or 98.9% of theory, based on chlorine. The selectivity with respect to the formation of EDC was accordingly 96.9%, based on ethylene, or 97.3% based on chlorine. The catalyst displayed no signs of exhaustion, even after an operating time of more than 1 year.

COMPARISON EXAMPLE 2

The catalyst was prepared as in Example 1 by impregnation of a spherical oxychlorination catalyst which contained 10% by weight of copper II chloride and 3.5 by weight of potassium chloride with 10% by weight of iron III chloride, and was packed analogously to Example 2, diluted with "Norton 704", into the chlorination reactor according to the loading pattern.

The same gas stream from the oxychlorination as described in Example 2 was reacted with chlorine, under analogous conditions, and subsequently cooled. The following amounts of condensate and waste gas were produced in this case:
3,086 kg/h of organic condensate
8,305 Nm³/h of waste gas for combustion
Composition of the organic condensate:
97.13% by weight 1,2-dichloroethane
0.75% by weight 1,1,2-trichloroethane
0.85% by weight ethyl chloride
0.03% by weight trans-1,2-dichloroethylene
0.02% by weight 1,1-dichloroethane
0.02% by weight cis-1,2-dichloroethylene
0.08% by weight chloroform
0.16% by weight carbon tetrachloride
0.57% by weight chloral
0.32% by weight 2-chloroethanol
0.018% by weight 2,2-dichloroethanol
0.003% by weight 2,2,2-trichloroethanol
0.05% by weight 2,2'-dichlorodiethyl ether
0.009% by weight bis-2-chloroethoxyethane
Composition of the waste gas:
94.35% by volume nitrogen
0.8% by volume carbon monoxide
0.9% by volume carbon dioxide
3.4% by volume oxygen
0.18% by volume ethyl chloride
Composition of the waste gas:
0.17% by volume 1,2-dichloroethane
0.06% by volume hydrogen chloride
0.10% by volume ethylene
0.01% by volume chlorine From this, conversions of 99.88%, based on chlorine, or 98.9%, based on ethylene, were calculated and the yields were 95.9% of theory, based on chlorine, and 95.5% of theory, based on ethylene. The selectivity with respect to the formation of EDC was 91.9%, based on ethylene, and 92.2%, based on chlorine. After an operating time of 8 months, a gradually progressing catalyst exhaustion could be detected since there is taking place an excursion of, both chlorine and ethylene into the waste gas from the chlorination reactor to an ever increasing extent.

EXAMPLE 3

The catalyst of Example 2 was used with an analogous loading pattern to that described in Example 2. 350 kmol/h of hydrogen chloride, 193 kmol/h of ethylene and 480 kmol/h of air were reacted under oxychlorination conditions to form EDC and water. After condensation of the organic reaction products at 45° C. and an absolute pressure of 4.5 bar, a 9,950 m³/h (based on standard conditions) residual gas stream of the following composition remained:
3.8% by volume ethylene
2.5% by volume $O_2$
2.2% by volume water vapors
0.5% by volume carbon monoxide
0.4% by volume carbon dioxide
4% by volume EDC vapor
0.4% by volume ethyl chloride vapor
85.2% by volume $N_2$.

This gas stream was pre-warmed to 110° C. and reacted with 16.8 kmol/h of chlorine ($C_2H_4$: $Cl_2$ = 1.006, molar) and the reaction was carried out in the same reactor as described in Example 2, i.e. at a space velocity, relative to standard conditions (0° C., 1,013 hPa) of about 2,580 $h^{-1}$, maximum temperatures of about 165° C. being produced in the catalyst bed. After cooling to 40° C. and −25° C., respectively a condensate of the following composition was produced:
98.55% by weight 1,2-dichloroethane
0.23% by weight 1,1,2-trichloroethane
0.46% by weight ethyl chloride
0.004% by weight trans-1,2-dichloroethylene
0.01% by weight 1,1-dichloroethane
0.006% by weight cis-1,2-dichloroethylene
0.06% by weight chloroform
0.10% by weight carbon tetrachloride
0.38% by weight chloral
0.18% by weight 2-chloroethanol
0.008% by weight 2,2-dichloroethanol
0.002% by weight 2,2,2-trichloroethanol
<10 ppm by weight 2,2'-dichlorodiethyl ether
<1 ppm by weight bis-2-chloroethoxyethane

COMPARISON EXAMPLE 3

The catalyst of Comparison Example 2 was used with analogous dilution. Analogously to Example 3, the waste gas stream from the oxychlorination described there was reacted with chlorine in the catalyst bed in the chlorination reactor of Example 2 at maximum temperatures of 165° C. After cooling and condensation, a condensate of the following composition was produced:
97.80% by weight 1,2-dichloroethane
0.26% by weight 1,1,2-trichloroethane
0.68% by weight ethyl chloride
0.028% by weight trans-1,2-dichloroethylene
0.016% by weight 1,1-dichloroethane
0.018% by weight cis-1,2-dichloroethylene
0.056% by weight chloroform
0.15% by weight carbon tetrachloride
0.48% by weight chloral
0.42% by weight 2-chloroethanol
0.025% by weight 2,2-dichloroethanol
0.007% by weight 2,2,2-trichloroethanol 0.07% by weight 2,2'-dichlorodiethyl ether
0.012% by weight bis-2-chloroethoxyethane From Examples 2 and 3, it can be seen that, inspite of increasing the catalyst temperature, the formation of by-products surprisingly only increased insignificantly when using the catalysts of the invention. Example 2 also shows the superiority with respect to conversion, yield and selectivity (see Comparison Example 2) of the process of the invention compared to the prior art.

TABLE 1

(catalysts according to the invention)

| Exper. | Catalyst composition | | | support material specific surface area in m²/g | Pre-warming temperature in °C. | Composition of the reaction gas from the oxychlorination in % by volume | | | |
|---|---|---|---|---|---|---|---|---|---|
| | active component in % by weight | additive in % by weight | Type | | | $C_2H_4$ | $H_2O$ | $N_2$ | $O_2$ |
| A | 10% $MnCl_2$ | — | $\gamma$-$Al_2O_3$ | 190 | 105 | 3.6 | 4.0 | 89.4 | 3.0 |
| B | 10% $CoCl_2$ | — | $\gamma$-$Al_2O_3$ | 190 | 105 | 12.0 | 4.0 | 81.0 | 3.0 |
| C | 10% NiO | — | $\gamma$-$Al_2O_3$ | 190 | 155 | 6.5 | 4.0 | 86.5 | 3.0 |
| D | 10% $MnCl_2$ 10% CoO | — | $SiO_2$ | 160 | 155 | 8.0 | 4.0 | 85.0 | 3.0 |
| E | 12% $MnCl_2$ | 10% $CuCl_2$ 3.5% KCl | $\gamma$-$Al_2O_3$ | 170 | 105 | 12.0 | 4.0 | 81.0 | 3.0 |
| F | 5% $MnCl_2$ 5% $CoCl_2$ 5% $NiCl_2$ | — | Al silicate | 130 | 105 | 7.0 | 4.0 | 86.0 | 3.0 |
| G | 10% $CoCl_2$ | 5% $BaCl_2$ | $SiO_2$ | 160 | 105 | 12.0 | 4.0 | 81.0 | 3.0 |
| H | 10% $MnCl_2$ | 5% KCl | $\gamma$-$Al_2O_3$ | 190 | 155 | 6.5 | 4.0 | 86.5 | 3.0 |
| J | 10% $NiCl_2$ | 10% $CuCl_2$ | $SiO_2$ | 160 | 105 | 10.0 | 4.0 | 83.0 | 3.0 |

| Exper. | Addition of HCl to the gas in %, relative to the $C_2H_4$ content | Composition of the condensate in % by weight | | | | | |
|---|---|---|---|---|---|---|---|
| | | Ethyl chloride | Chloral | 2-Chloro-ethanol | 2,2-Dichloro-ethanol | 2,2,2-Trichloro-ethanol | 2,2'-Dichloro-diethyl | Bis-2-chloro-ethoxyethane |
| A | — | 0.005 | 0.50 | 0.45 | 0.018 | 0.004 | 0.0010 | 0.0001 |
| B | — | 0.004 | 0.42 | 0.34 | 0.013 | 0.003 | 0.0010 | 0.0001 |
| C | — | 0.002 | 0.53 | 0.47 | 0.019 | 0.005 | 0.0010 | 0.0001 |
| D | — | 0.004 | 0.40 | 0.30 | 0.012 | 0.002 | 0.0010 | 0.0001 |
| E | — | 0.003 | 0.46 | 0.36 | 0.014 | 0.003 | 0.0010 | 0.0001 |
| F | — | 0.002 | 0.42 | 0.33 | 0.013 | 0.002 | 0.0010 | 0.0001 |
| G | — | 0.004 | 0.48 | 0.37 | 0.014 | 0.004 | 0.0010 | 0.0001 |
| H | — | 0.005 | 0.50 | 0.44 | 0.016 | 0.004 | 0.0010 | 0.0001 |
| J | — | 0.003 | 0.51 | 0.43 | 0.016 | 0.003 | 0.0010 | 0.0001 |

Note: As shown by the results of Experiments C, D and H, increased prior pre-warming according to German Offenlegungsschrift 2,733,502 brings no additional effects when using the catalysts according to the invention.

TABLE 2

(state of the art)

| Exper. | Catalyst composition | | | support material specific surface area in m²/g | Pre-warming temperature in °C. | Composition of the reaction gas from the oxychlorination in % by volume | | | |
|---|---|---|---|---|---|---|---|---|---|
| | active component in % by weight | additive in % by weight | Type | | | $C_2H_4$ | $H_2O$ | $N_2$ | $O_2$ |
| K | — | — | $\gamma$-$Al_2O_3$ | 190 | 105 | 3.5 | 4.0 | 89.5 | 3.0 |
| L | — | — | $\gamma$-$Al_2O_3$ | 190 | 155 | 3.5 | 4.0 | 89.5 | 3.0 |
| M | — | — | $\gamma$-$Al_2O_3$ | 190 | 155 | 8.0 | 4.0 | 85.0 | 3.0 |
| N | — | — | $\gamma$-$Al_2O_3$ | 190 | 105 | 8.0 | 4.0 | 85.0 | 3.0 |
| O | — | — | $\gamma$-$Al_2O_3$ | 190 | 155 | 12.0 | 4.0 | 81.0 | 3.0 |
| P | 10% $CuCl_2$ | — | $\gamma$-$Al_2O_3$ | 190 | 105 | 6.0 | 4.0 | 87.0 | 3.0 |
| Q | 10% $FeCl_3$ | — | $\gamma$-$Al_2O_3$ | 190 | 105 | 4.0 | 4.0 | 89.0 | 3.0 |
| R | 10% $CuCl_2$ 10% $FeCl_3$ | 2% KCl | $\gamma$-$Al_2O_3$ | 190 | 105 | 4.0 | 4.0 | 89.0 | 3.0 |
| S | 10% $FeCl_3$ | 2% KCl | $\gamma$-$Al_2O_3$ | 190 | 105 | 6.0 | 4.0 | 87.0 | 3.0 |

| Exper. | Addition of HCl to the gas in %, relative to the $C_2H_4$ content | Composition of the condensate in % by weight | | | | | | |
|---|---|---|---|---|---|---|---|---|
| | | Ethyl chloride | Chloral | 2-Chloro-ethanol | 2,2-Dichloro-ethanol | 2,2,2-Trichloro-ethanol | 2,2'-Dichloro-diethyl | Bis-2-chloro-ethoxyethane |
| K | — | 0.004 | 1.57 | 5.68 | 0.22 | 0.057 | 0.025 | 0.0010 |
| L | — | 0.003 | 0.51 | 0.71 | 0.036 | 0.008 | 0.005 | 0.0004 |
| M | — | 0.005 | 1.37 | 4.56 | 0.18 | 0.044 | 0.021 | 0.0008 |
| N | 20% | 0.004 | 0.95 | 2.45 | 0.10 | 0.021 | 0.012 | 0.0005 |
| O | 20% | 0.006 | 1.11 | 2.40 | 0.11 | 0.020 | 0.011 | 0.0006 |
| P | — | 0.015 | 0.98 | 0.78 | 0.030 | 0.009 | 0.004 | 0.0005 |
| Q | — | 0.020 | 0.62 | 0.58 | 0.029 | 0.008 | 0.003 | 0.0004 |
| R | — | 0.019 | 0.75 | 0.63 | 0.031 | 0.010 | 0.005 | 0.0006 |

TABLE 2-continued (state of the art)

| | | | | | | | | |
|---|---|---|---|---|---|---|---|---|
| S | — | 0.022 | 0.60 | 0.55 | 0.028 | 0.009 | 0.004 | 0.0007 |

Note:
Experiment K corresponds to DE-B-1,793,051
Experiments L and M correspond to DE-A-2,733,502
Experiments P, Q, R, and S correspond to DE-A-2,649,533
Experiments N and O correspond to DE-A-2,831,539 and DE-A-2,733,502 respectively Various modifications of the process may be made without departing from the spirit or scope thereof and it is to be understood that the invention is intended to be limited only as defined in the appended claims.

What we claim is:

1. In a process for preparation of 1,2-dichloroethane by chlorination of ethylene-containing reaction vent gases from the oxychlorination of ethylene in the presence of a catalyst carrier impregnated with metal compounds wherein the waste gases from the oxychlorination stage are chlorinated, the improvement comprising preheating the ethylene containing waste gases to at least 50° C. and then chlorinating the ethylene at 100° C. to 300° C. at a pressure of 1 to 7 bar with a space velocity of 100 to 5000 $h^{-1}$ related to standard conditions in the presence of at least one metal compound selected from the group consisting of chlorides and oxides of manganese, nickel and cobalt supported on a catalyst carrier.

2. The process of claim 1 wherein the concentration of the metal chlorides and oxides on the catalyst support is 1 to 30% by weight based on the carrier.

3. The process of claim 1 wherein the carrier is made of at least one member of the group consisting of activated aluminum oxide, hydrated aluminum oxide, silica gel and aluminum silicate.

4. The process of claim 1 wherein the catalyst carrier has a specific surface area by BET of 20 to 200 $m^2/g$.

5. The process of claim 1 wherein the catalyst contains up to 20% by weight of copper II chloride and/or 0.5 to 10% by weight of alkali metal or alkaline earth metal chlorides, based on the weight of the carrier.

6. The process of claim 1 wherein the waste gas contains 2 to 12% by volume of ethylene.

* * * * *

UNITED STATES PATENT AND TRADEMARK OFFICE
CERTIFICATE OF CORRECTION

PATENT NO. : 4,754,088
DATED : June 28, 1988
INVENTOR(S) : Ludwig Schmidhammer et al It is certified that error appears in the above-identified patent and that said Letters Patent is hereby corrected as shown below:

Column 5, lines 17 and 18 "and-/or" should be --and/or--.

Signed and Sealed this

First Day of August, 1989

Attest:

DONALD J. QUIGG

Attesting Officer

Commissioner of Patents and Trademarks

UNITED STATES PATENT AND TRADEMARK OFFICE
CERTIFICATE OF CORRECTION

PATENT NO. : 4,754,088

DATED : June 28, 1988

INVENTOR(S) : Ludwig Schmidhammer et al

It is certified that error appears in the above-identified patent and that said Letters Patent is hereby corrected as shown below:

On the title page insert Foreign Application Priority Data

--- March 11, 1986    German    3608043 ---.

Signed and Sealed this

Twenty-seventh Day of March, 1990

Attest:

JEFFREY M. SAMUELS

*Attesting Officer*    *Acting Commissioner of Patents and Trademarks*